US011150641B2

(12) United States Patent
Cermak et al.

(10) Patent No.: US 11,150,641 B2
(45) Date of Patent: Oct. 19, 2021

(54) SYSTEM AND METHOD TO INITIATE REMOTE CONTROL OF AN AUTONOMOUS VEHICLE

(71) Applicant: GENERAL MOTORS LLC, Detroit, MI (US)

(72) Inventors: Alexander X. Cermak, Grosse Pointe Woods, MI (US); Esteban Camacho, Belleville, MI (US); Dexter C. Lowe, Macomb, MI (US); Ryan Olejniczak, Macomb, MI (US)

(73) Assignee: GENERAL MOTORS LLC, Detroit, MI (US)

( * ) Notice: Subject to any disclaimer, the term of this patent is extended or adjusted under 35 U.S.C. 154(b) by 229 days.

(21) Appl. No.: 16/448,015

(22) Filed: Jun. 21, 2019

(65) Prior Publication Data

US 2020/0401126 A1 Dec. 24, 2020

(51) Int. Cl.
| | | |
|---|---|---|
| *G05D 1/00* | (2006.01) | |
| *G07C 5/00* | (2006.01) | |
| *G07C 5/02* | (2006.01) | |
| *G07C 5/08* | (2006.01) | |
| *B60W 50/08* | (2020.01) | |
| *B60W 60/00* | (2020.01) | |
| *A61B 5/18* | (2006.01) | |

(52) U.S. Cl.
CPC ............. *G05D 1/0011* (2013.01); *A61B 5/18* (2013.01); *G07C 5/02* (2013.01); *G07C 5/08* (2013.01)

(58) Field of Classification Search
CPC ............. G05D 1/0011; G05D 1/0022; G05D 2201/0213; G05D 5/00; G05D 1/00; A61B 5/18; G07C 5/08; G07C 5/02; G07C 5/0808; G07C 5/008; G07C 5/00; G08G 1/16; B60W 50/00; B60W 50/082; B60W 2540/00; B60W 60/00; B60K 28/00; B60K 28/02; B60K 28/04; B60K 28/06

See application file for complete search history.

(56) References Cited

U.S. PATENT DOCUMENTS

| | | | | |
|---|---|---|---|---|
| 8,725,311 | B1 * | 5/2014 | Breed | A61B 5/0507 |
| | | | | 701/1 |
| 8,874,301 | B1 * | 10/2014 | Rao | B60K 28/04 |
| | | | | 701/25 |
| 10,328,897 | B1 * | 6/2019 | Nabbe | G06F 21/305 |
| 2010/0030434 | A1 * | 2/2010 | Okabe | A61B 5/18 |
| | | | | 701/48 |

(Continued)

FOREIGN PATENT DOCUMENTS

| | | | |
|---|---|---|---|
| WO | 2018097423 A1 | 5/2018 | |
| WO | 2018179777 A1 | 10/2018 | |
| WO | 2019032088 A1 | 2/2019 | |

OTHER PUBLICATIONS

U.S. Appl. No. 16/240,945, filed Jan. 7, 2019.

*Primary Examiner* — Yonel Beaulieu
(74) *Attorney, Agent, or Firm* — Lorenz & Kopf LLP (57) ABSTRACT

One general aspect includes a method to initiate remote control of a vehicle, the method including: receiving, via a processor, an indication that a manual drive sequence should be initiated by a remotely located data center; and based on the indication, via the processor, initiating the manual drive sequence such that the data center can remotely control the vehicle.

20 Claims, 4 Drawing Sheets

(56) References Cited

U.S. PATENT DOCUMENTS

| | | | |
|---|---|---|---|
| 2012/0123644 A1* | 5/2012 | Waldmann | B60T 7/042 701/45 |
| 2013/0179024 A1* | 7/2013 | Nordbruch | B60R 99/00 701/23 |
| 2014/0143839 A1* | 5/2014 | Ricci | H04N 21/25816 726/4 |
| 2014/0207535 A1* | 7/2014 | Stefan | G07C 5/008 705/7.42 |
| 2017/0243484 A1* | 8/2017 | Li | G08G 1/096725 |

* cited by examiner

SYSTEM AND METHOD TO INITIATE REMOTE CONTROL OF AN AUTONOMOUS VEHICLE

Autonomous vehicles take the work out of travelling. However, certain situations warrant that it is not very safe for theses vehicles to be driving themselves from one place to another. Moreover, such situations may not make it safe for one of the vehicle passengers to manually control the vehicle or the vehicle may not have the proper features for one of the passengers to take control of the vehicle's driving operations (e.g., when the autonomous vehicle does not have a steering wheel). It is therefore desirable to provide a system and method that initiates a particular manual drive sequence that allows an advisor of a remote data center to manually control the autonomous vehicle and safely drive the vehicle along difficult and/or dangerous terrain until reaching safety. Other desirable features and characteristics of the present invention will become apparent from the subsequent detailed description of the invention and the appended claims, taken in conjunction with the accompanying drawings and this background of the invention.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method to initiate remote control of a vehicle, the method including: receiving, via a processor, an indication that a manual drive sequence should be initiated by a remotely located data center; and based on the indication, via the processor, initiating the manual drive sequence such that the data center can remotely control the vehicle. Other embodiments of this aspect include corresponding computer systems, apparatus, and computer programs recorded on one or more computer storage devices, each configured to perform the actions of the methods.

Implementations may include one or more of the following features. The method where the manual drive sequence enables an advisor to remotely control the vehicle from the data center. The method where the indication is provided by a vehicle sensor module (VSM) of the vehicle, where the indication corresponds to a malfunctioning of one or more vehicle systems. The method where the indication is provided by a biometrics device configured to monitor the physical health of one or more vehicle passengers, where the indication corresponds to a failing health of the one or more vehicle passengers. The method where the biometrics device is included in a mobile computing device of the one or more vehicle passengers. The method where the indication is provided by one or more vehicle passengers via a button/control installed in the vehicle. The method where the indication is provided by an automated driving system (ADS), where the indication corresponds to the driving conditions of the environment surrounding the vehicle. Implementations of the described techniques may include hardware, a method or process, or computer software on a computer-accessible medium.

One general aspect includes a system to initiate remote control of a vehicle, the system including: a memory configured to include one or more executable instructions and a processor configured to execute the executable instructions, where the executable instructions enable the processor to carry out the following steps: receiving an indication that a manual drive sequence should be initiated by a remotely located data center; and based on the indication, initiating the manual drive sequence such that the data center can remotely control the vehicle. Other embodiments of this aspect include corresponding computer systems, apparatus, and computer programs recorded on one or more computer storage devices, each configured to perform the actions of the methods.

Implementations may include one or more of the following features. The system where the manual drive sequence enables an advisor to remotely control the vehicle from the data center. The system where the indication is provided by a vehicle sensor module (VSM) of the vehicle, where the indication corresponds to a malfunctioning of one or more vehicle systems. The system where the indication is provided by a biometrics device configured to monitor the physical health of one or more vehicle passengers, where the indication corresponds to a failing health of the one or more vehicle passengers. The system where the biometrics device is included in a mobile computing device of the one or more vehicle passengers. The system where the indication is provided by one or more vehicle passengers via a button/control installed in the vehicle. The system where the indication is provided by an automated driving system (ADS), where the indication corresponds to the driving conditions of the environment surrounding the vehicle. Implementations of the described techniques may include hardware, a method or process, or computer software on a computer-accessible medium.

One general aspect includes a non-transitory and machine-readable medium having stored thereon executable instructions adapted to initiate remote control of a vehicle, which when provided to a processor and executed thereby, causes the processor to carry out the following steps: receiving an indication that a manual drive sequence should be initiated by a remotely located data center; and based on the indication, initiating the manual drive sequence such that the data center can remotely control the vehicle. Other embodiments of this aspect include corresponding computer systems, apparatus, and computer programs recorded on one or more computer storage devices, each configured to perform the actions of the methods.

Implementations may include one or more of the following features. The non-transitory and machine-readable medium where the manual drive sequence enables an advisor to remotely control the vehicle from the data center. The non-transitory and machine-readable medium where the indication is provided by a vehicle sensor module (VSM) of the vehicle, where the indication corresponds to a malfunctioning of one or more vehicle systems. The non-transitory and machine-readable medium where the indication is provided by a biometrics device configured to monitor the physical health of one or more vehicle passengers, where the indication corresponds to a failing health of the one or more vehicle passengers. The non-transitory and machine-readable medium where the indication is provided by one or more vehicle passengers via a button/control installed in the vehicle. The non-transitory and machine-readable medium where the indication is provided by an automated driving system (ADS), where the indication corresponds to the driving conditions of the environment surrounding the vehicle. Implementations of the described techniques may include hardware, a method or process, or computer software on a computer-accessible medium.

The above features and advantages and other features and advantages of the present teachings are readily apparent from the following detailed description for carrying out the teachings when taken in connection with the accompanying drawings.

BRIEF DESCRIPTION OF THE DRAWINGS

The disclosed examples will hereinafter be described in conjunction with the following drawing figures, wherein like numerals denote like elements, and wherein.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present system and/or method. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present system and/or method. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The following detailed description is merely exemplary in nature and is not intended to limit the application and uses. Furthermore, there is no intention to be bound by any expressed or implied theory presented in the preceding background and brief summary or the following detailed description. As used herein, the term module refers to an application specific integrated circuit (ASIC), an electronic circuit, a processor (shared, dedicated, or group) and memory that executes one or more software or firmware programs or code segments, a combinational logic circuit, and/or other suitable components that provide the described functionality.

Figure 1:
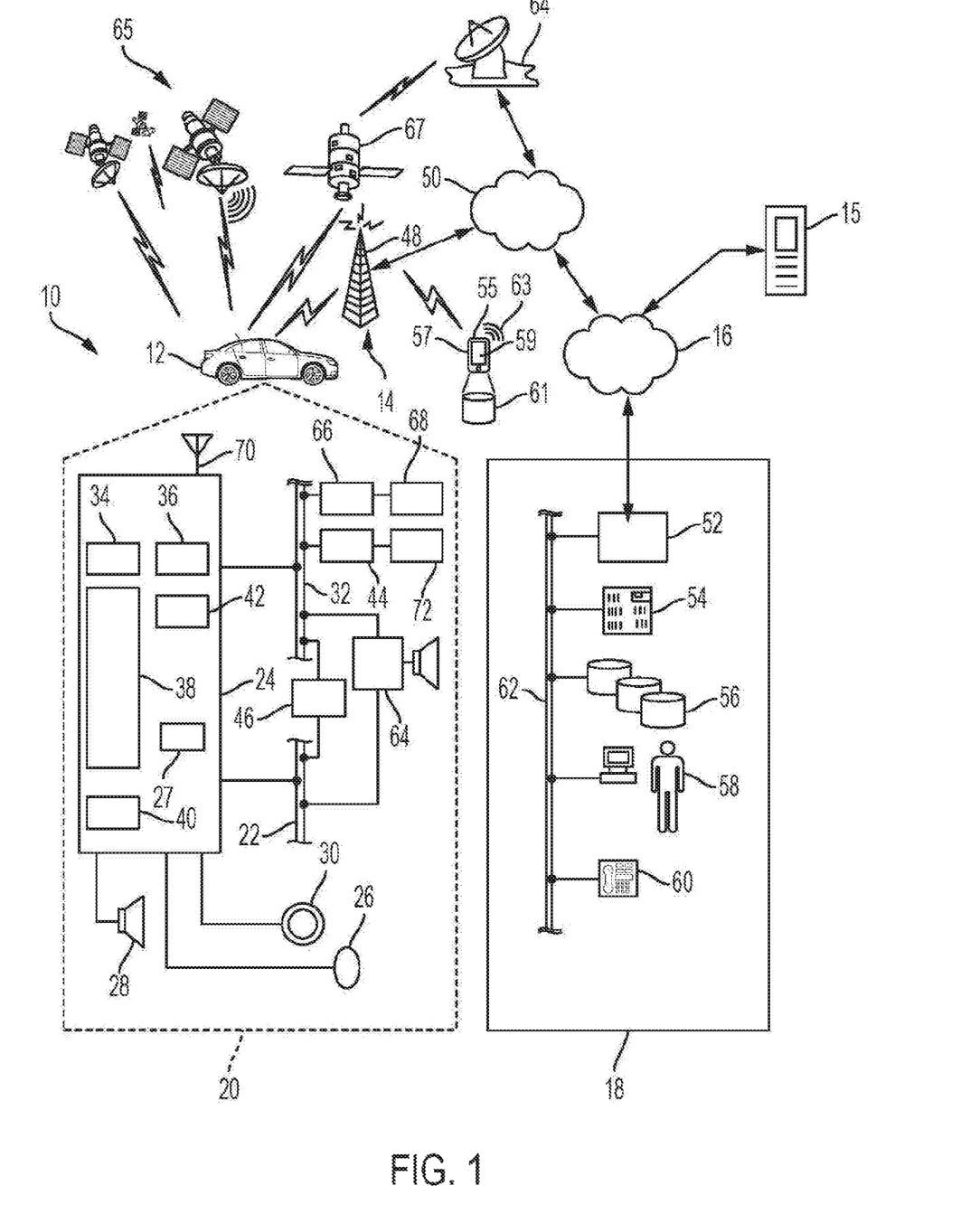
FIG. 1 is a block diagram depicting an exemplary embodiment of a communications system that is capable of utilizing the system and method disclosed herein.

As shown in FIG. 1, there is shown a non-limiting example of a communication system 10 that may be used together with examples of the system disclosed herein and/or to implement examples of the methods disclosed herein. Communication system 10 generally includes a fleet of vehicles 12, a wireless carrier system 14, a mobile computing device 57, a land network 16, and a data center 18 (i.e., the backend). It should be appreciated that the overall architecture, setup and operation, as well as the individual components of the illustrated system are merely exemplary and that differently configured communication systems may also be utilized to implement the examples of the system and/or method disclosed herein. Thus, the following paragraphs, which provide a brief overview of the illustrated communication system 10, are not intended to be limiting.

Each fleet vehicle 12 may be any type of autonomous vehicle (discussed below) such as a motorcycle, car, truck, bicycle, recreational vehicle (RV), boat, plane, etc., and is equipped with suitable hardware and software that enables it to communicate over communication system 10. In certain embodiments, each vehicle 12 may include a power train system with multiple generally known torque-generating devices including, for example, one or more electric motors or traction motors that convert electrical energy into mechanical energy for vehicle propulsion.

Some of the fundamental vehicle hardware 20 for each fleet vehicle is shown generally in FIG. 1 including a telematics unit 24, a microphone 26, speaker 28, and buttons and/or controls 30 connected to telematics unit 24. Operatively coupled to telematics unit 24 is a network connection or vehicle bus 32. Examples of suitable network connections include a controller area network (CAN), a media oriented system transfer (MOST), a local interconnection network (LIN), an Ethernet, dedicated short-range communications channel (DSRC), and other appropriate connections such as those that conform with known ISO (International Organization for Standardization), SAE (Society of Automotive Engineers), and/or IEEE (Institute of Electrical and Electronics Engineers) standards and specifications, to name a few.

The telematics unit 24 is a communication system which provides a variety of services through its communications with the data center 18, and generally includes an electronic processing device 38, one or more types of electronic memory 40, a cellular chipset/component 34, wireless modem 36, dual mode antenna 70, and navigation unit containing a GPS chipset/component 42 capable of communicating location information via a GPS satellite system 65. GPS component 42 thus receives coordinate signals from a constellation of GPS satellites 65. From these signals, the GPS component 42 can determine vehicle position, which may be used for providing navigation and other position-related services to the vehicle operator. Navigation information can be presented on a display of telematics unit 24 (or other display within the vehicle) or can be presented verbally such as is done when supplying turn-by-turn navigation. The navigation services can be provided using a dedicated in-vehicle navigation module (which can be part of GPS component 42), or some or all navigation services can be done via telematics unit 24, wherein the location coordinate information is sent to a remote location for purposes of providing the vehicle with navigation maps, map annotations, route calculations, and the like.

The telematics unit 24 may provide various services including: turn-by-turn directions and other navigation-related services provided in conjunction with the GPS component 42; airbag deployment notification and other emergency or roadside assistance-related services provided in connection with various crash and/or collision sensor interface modules 66 and collision sensors 68 located throughout the vehicle and/or infotainment-related services where music, internet web pages, movies, television programs, videogames, and/or other content are downloaded by an infotainment center 46 operatively connected to the telematics unit 24 via vehicle bus 32 and audio bus 22. In one example, downloaded content is stored for current or later playback. The above-listed services are by no means an exhaustive list of all the capabilities of telematics unit 24, but are simply an illustration of some of the services telematics unit 24 may be capable of offering. It is anticipated that telematics unit 24 may include a number of additional components in addition to and/or different components from those listed above.

Vehicle communications may use radio transmissions to establish a voice channel with wireless carrier system 14 so that both voice and data transmissions can be sent and received over the voice channel. Vehicle communications are enabled via the cellular component 34 for voice communications and the wireless modem 36 for data transmission. Any suitable encoding or modulation technique may be used with the present examples, including digital transmission technologies, such as TDMA (time division multiple access), CDMA (code division multiple access), W-CDMA (wideband CDMA), FDMA (frequency division multiple access), OFDMA (orthogonal frequency division multiple access), etc. To accomplish this effect, dual mode antenna 70 services the GPS component 42 and the cellular component 34.

Microphone 26 provides the driver or other vehicle occupant with a means for inputting verbal or other auditory commands, and can be equipped with an embedded voice processing unit utilizing a human/machine interface (HMI) technology known in the art. Conversely, speaker 28 provides audible output to the vehicle occupants and can be either a stand-alone speaker specifically dedicated for use with the telematics unit 24 or can be part of a vehicle audio component 64. In either event, microphone 26 and speaker 28 enable vehicle hardware 20 and data center 18 to communicate with the occupants through audible speech. The vehicle hardware also includes one or more buttons and/or controls 30 for enabling a vehicle occupant to activate or engage one or more of the vehicle hardware components 20. For example, one of the buttons and/or controls 30 can be an electronic pushbutton used to initiate voice communication with data center 18 (whether it be a human such as advisor 58 or an automated call response system). In another example, one of the buttons and/or controls 30 can be used to initiate emergency services.

The audio component 64 is operatively connected to the vehicle bus 32 and the audio bus 22. The audio component 64 receives analog information, rendering it as sound, via the audio bus 22. Digital information is received via the vehicle bus 32. The audio component 64 provides amplitude modulated (AM) and frequency modulated (FM) radio, compact disc (CD), digital video disc (DVD), and multimedia functionality independent of the infotainment center 46. Audio component 64 may contain a speaker system or may utilize speaker 28 via arbitration on vehicle bus 32 and/or audio bus 22.

The vehicle crash and/or collision detection sensor interface 66 is operatively connected to the vehicle bus 32. The collision sensors 68 provide information to telematics unit 24 via the crash and/or collision detection sensor interface 66 regarding the severity of a vehicle collision, such as the angle of impact and the amount of force sustained.

Vehicle sensors 72, connected to various vehicle sensor modules 44 (VSMs) in the form of electronic hardware components located throughout each fleet vehicle and use the sensed input to perform diagnostic, monitoring, control, reporting and/or other functions. Each of the VSMs 44 is preferably connected by vehicle bus 32 to the other VSMs, as well as to the telematics unit 24, and can be programmed to run vehicle system and subsystem diagnostic tests. As examples, one VSM 44 can be an engine control module (ECM) that controls various aspects of engine operation such as fuel ignition and ignition timing. According to one embodiment, the ECM is equipped with on-board diagnostic (OBD) features that provide myriad real-time data, such as that received from various sensors including vehicle emissions sensors, fuel diagnostics sensors, and vehicle oil pressure sensors as well as provide a standardized series of diagnostic trouble codes (DTCs) which allow a technician to rapidly identify and remedy malfunctions within the vehicle. VSM 44 can similarly be a powertrain control module (PCM) that regulates operation of one or more components of the powertrain system. Another VSM 44 can be a body control module (BCM) that monitors and governs various electrical components located throughout the vehicle body like the vehicle's power door locks, air conditioner, tire pressure, lighting system, engine ignition, vehicle seat adjustment and heating, mirrors, and headlights. Furthermore, as can be appreciated by skilled artisans, the above-mentioned VSMs are only examples of some of the modules that may be used the vehicles 12, as numerous others are also possible.

Wireless carrier system 14 may be a cellular telephone system or any other suitable wireless system that transmits signals between the vehicle hardware 20 and land network 16. According to an example, wireless carrier system 14 includes one or more cell towers 48.

Land network 16 can be a conventional land-based telecommunications network connected to one or more landline telephones, and that connects wireless carrier system 14 to data center 18. For example, land network 16 can include a public switched telephone network (PSTN) and/or an Internet protocol (IP) network, as is appreciated by those skilled in the art. Of course, one or more segments of the land network 16 can be implemented in the form of a standard wired network, a fiber or other optical network, a cable network, other wireless networks such as wireless local networks (WLANs) or networks providing broadband wireless access (BWA), or any combination thereof.

As revealed above, one of the networked devices that can directly or indirectly communicate with the telematics unit 24 is a mobile computing device 57, such as (but not limited to) a smart phone, personal laptop computer or tablet computer having two-way communication capabilities, a wearable computer such as (but not limited to) a smart watch or glasses, or any suitable combinations thereof. The mobile computing device 57 can include computer processing capability, biometrics sensing devices, and a transceiver 53 capable of communicating with remote locations (e.g., data center 18). Examples of the mobile computing device 57 include the iPhone™ and Apple Watch™ each being manufactured by Apple, Inc. and the Droid™ smart phone manufactured by Motorola, Inc. as well as others.

Mobile device 57 may be used inside or outside of a vehicle and may be coupled to the vehicle by wire or wirelessly. Mobile device 57 may also be configured to provide services according to a subscription agreement with a third-party facility or wireless/telephone service provider. It should be appreciated that various service providers may utilize the wireless carrier system 14 and that the service provider of telematics unit 24 may not necessarily be the same as the service provider of mobile device 57. When using a short-range wireless connection (SRWC) protocol (e.g., Bluetooth Low Energy, Wi-Fi, etc.), mobile computing device 57 and telematics unit 24 may pair with each other (or link to one another) on a case-by-case basis and while within a wireless range; SRWC pairing is known to skilled artisans. The SRWC protocol may be an aspect of telematics unit 24 or may be part of one or more independent VSMs 44 such as the PEPS and/or BCM 44. Once SRWC is established, the devices may be considered bonded (i.e., they may recognize one another and/or connect automatically when they are in a predetermined proximity or range of one other. In other words—they may become, at least temporarily, network participants).

The biometrics sensing devices can be configured to detect a health level of a vehicle passenger and provide health information to the processing capabilities of the mobile computing device 57. The biometrics sensing devices may include one or more of an infrared sensor, a near infrared tissue spectrometry sensor, an electrochemical sensor, a heart rate sensor, a blood pressure sensor, a laser sensor, a motion detector, and a behavioral sensor, etc. In particular, the behavioral sensor may detect health behavior based on one or more from among a vehicle passenger's movements. According to yet another exemplary embodiment, a laser sensor may transmit a laser to ping the dermis and excite molecules of foreign substances (e.g., poisons, narcotics, etc.). The laser may then be used to measure the amount of these foreign substances present in capillary blood.

Data center 18 is designed to provide the vehicle hardware 20 with a number of different system backend functions and, according to the example shown here, generally includes one or more switches 52, servers 54, databases 56, advisors 58 as well as a variety of other telecommunication/computer equipment 60. These various data center components are suitably coupled to one another via a network connection or bus 62, such as the one previously described in connection with the vehicle hardware 20. Switch 52, which can be a private branch exchange (PBX) switch, routes incoming signals so that voice transmissions are usually sent to either advisor 58 or an automated response system, and data transmissions are passed on to a modem or other piece of telecommunication/computer equipment 60 for demodulation and further signal processing. The modem or other telecommunication/computer equipment 60 may include an encoder, as previously explained, and can be connected to various devices such as a server 54 and database 56. Although the illustrated example has been described as it would be used in conjunction with a manned data center 18, it will be appreciated that the data center 18 can be any central or remote facility, manned or unmanned, mobile or fixed, to or from which it is desirable to exchange voice and data.

Advisors 58 will also have the ability to remotely control vehicle 12 from data center 18. This remote controlling ability will allow at least one of the advisors 58 to take control of vehicle 12, for example, when vehicle 12 realizes it is in an area considered unsafe for autonomous driving, when one or more of the VSMs 44 indicates some kind of malfunction, when a vehicle passenger requests the advisors 58 take control of vehicle 12, and/or when a biometrics device indicates one of the vehicle passenger's is having health issues (discussed below). In order to take control of vehicle 12, an advisor 58 will initiate a third-party manual drive sequence which allows the advisor 58 to both control the vehicle 12 and communicate with one or more vehicle passengers simultaneously. The biometric device that monitors one or more vehicle passengers can be installed in the vehicle 12 (as a VSM 44) or it can be part of a wearable smart device worn on one of the vehicle passengers, which is in direct/indirect communications with the vehicle 12 (i.e., via telematics unit 24).

Server 54 can incorporate a data controller which essentially controls its operations. Server 54 may control data information as well as act as a transceiver to send and/or receive the data information (i.e., data transmissions) from one or more of the databases 56, and telematics unit 24. The controller is moreover capable of reading executable instructions stored in a non-transitory machine readable medium and may include one or more from among a processor, microprocessor, central processing unit (CPU), graphics processor, Application Specific Integrated Circuits (ASICs), Field-Programmable Gate Arrays (FPGAs), state machines, and a combination of hardware, software, and firmware components.

Computer 15 can be one of a number of computers accessible via a private or public network such as the Internet. Each such computer 15 can be used for one or more purposes, such as a web server accessible by the vehicle via wireless carrier 14. Other such accessible computers 15 can be, for example: a service center computer (e.g., a SIP Presence server) where diagnostic information and other vehicle data can be uploaded from the vehicle via the telematics unit 24; a client computer used by the vehicle owner or other subscriber for such purposes as accessing or receiving vehicle data or to setting up or configuring subscriber preferences or controlling vehicle functions; or a third party repository to or from which vehicle data or other information is provided, whether by communicating with a vehicle 12 or data center 18. Computer 15 can also be used for providing Internet connectivity such as DNS services or as a network address server that uses DHCP or other suitable protocol to assign an IP address to the vehicle 12.

Computer 15 could be designed to store a variety of application program interface (API) suites 99. Moreover, in certain instances, these API suites 99 may be accessible to the data center 18, or one or more third parties. As examples, one API suite 99 can be a weather API configured to allow a user to see the weather at a selected location (e.g., the environment surrounding vehicle 12). Another API suite 99 can be a roadwork API configured to provide one or more digital maps of roadway sections containing reduced speed zones, construction sites, lane closures, and/or traffic congestion related issues.

Autonomous Vehicle Aspects

Figure 2:
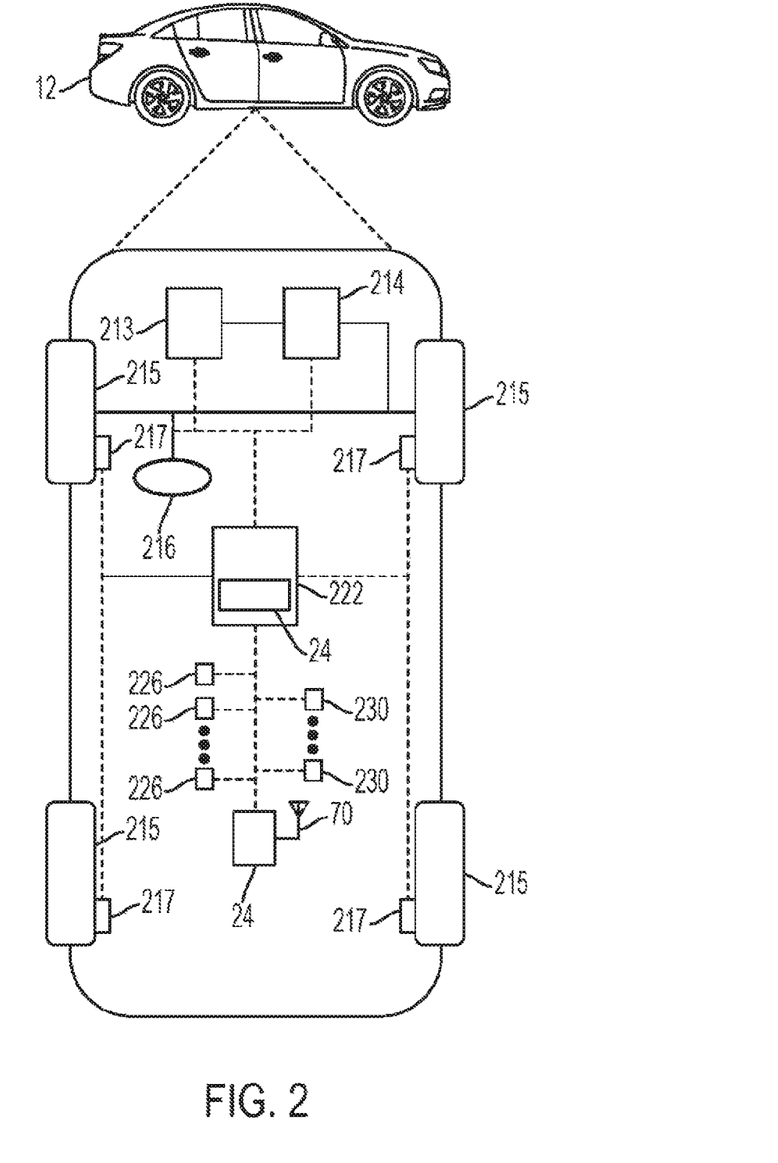
FIG. 2 is a schematic diagram of an autonomously controlled vehicle, according to an embodiment of the communications system of FIG. 1.

With reference to FIG. 2, each fleet vehicle 12 can be an autonomous vehicle (AV) that generally includes a transmission 214 which may be installed to transmit power from propulsion system 213 to vehicle wheels 215 according to selectable speed ratios. According to various embodiments, transmission 214 may include a step-ratio automatic transmission, a continuously-variable transmission, or other appropriate transmission. Fleet vehicle 12 additionally includes wheel brakes 217 configured to provide braking torque to the vehicle wheels 215. The wheel brakes 217 may, in various embodiments, include friction brakes, a regenerative braking system such as an electric machine, and/or other appropriate braking systems. It should be understood transmission 214 does not necessarily need to be installed for propulsion system 213 to propel fleet vehicle 12.

Each fleet vehicle 12 additionally includes a steering system 216. While depicted as including a steering wheel for illustrative purposes, in some contemplated embodiments, the steering system 216 may not include a steering wheel. Telematics unit 24 is additionally configured to wirelessly communicate with other vehicles ("V2V") and/or infrastructure ("V2I") and/or pedestrians ("V2P"). These communications may collectively be referred to as a vehicle-to-entity communication ("V2X"). In an exemplary embodiment, this communication system communicates via at least one dedicated short-range communications (DSRC) channel. DSRC channels refer to one-way or two-way short-range to medium-range wireless communication channels specifically designed for automotive use and a corresponding set of protocols and standards.

The propulsion system 213 (explained above), transmission 214, steering system 216, and wheel brakes 217 are in communication with or under controls device 222. Vehicle controls device 222 includes an automated driving system (ADS) 224 for automatically controlling various actuators in the vehicle. In an exemplary embodiment, ADS 224 is a so-called Level Four or Level Five automation system. A Level Four system indicates "high automation", referring to the driving mode-specific performance by an automated driving system of all aspects of the dynamic driving task, even if a human driver does not respond appropriately to a request to intervene. A Level Five system indicates "full automation", referring to the full-time performance by an automated driving system of all aspects of the dynamic driving task under all roadway and environmental conditions that can be managed by a human driver. In an exemplary embodiment, the ADS 224 is configured to communicate automated driving information with and control propulsion system 213, transmission 214, motors 219, steering system 216, and wheel brakes 217 to control vehicle acceleration, steering, and braking, respectively, without human intervention via a plurality of actuators 230 in response to inputs from a plurality of driving sensors 226, which may include GPS, RADAR, LIDAR, optical cameras, thermal cameras, ultrasonic sensors, and/or additional sensors as appropriate.

Figure 3:
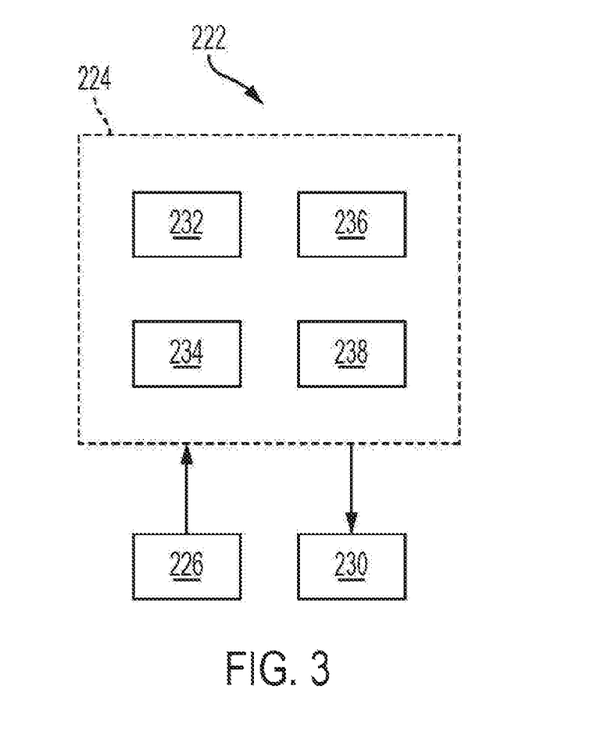
FIG. 3 is a schematic block diagram of an exemplary automated driving system (ADS) for the vehicle of FIG. 2.

In various embodiments, the instructions of the ADS 224 may be organized by function or system. For example, as shown in FIG. 3, ADS 224 can include a sensor fusion system 232 (computer vision system), a positioning system 234, a guidance system 236, and a vehicle control system 238. As can be appreciated, in various embodiments, the instructions may be organized into any number of systems (e.g., combined, further partitioned, etc.) as the disclosure is not limited to the present examples.

In various embodiments, the sensor fusion system 232 synthesizes and processes sensor data and predicts the presence, location, classification, and/or path of objects and features of the environment of the vehicle 12. In various embodiments, the sensor fusion system 232 can incorporate information from multiple sensors, including but not limited to cameras, lidars, radars, and/or any number of other types of sensors. In one or more exemplary embodiments described herein, the sensor fusion system 232 supports or otherwise performs the ground reference determination processes and correlates image data to lidar point cloud data, the vehicle reference frame, or some other reference coordinate frame using calibrated conversion parameter values associated with the pairing of the respective camera and reference frame to relate lidar points to pixel locations, assign depths to the image data, identify objects in one or more of the image data and the lidar data, or otherwise synthesize associated image data and lidar data. In other words, the sensor output from the sensor fusion system 232 provided to the vehicle control system 238 (e.g., indicia of detected objects and/or their locations relative to the vehicle 12) reflects or is otherwise influenced by the calibrations and associations between camera images, lidar point cloud data, and the like.

The positioning system 234 processes sensor data along with other data to determine a position (e.g., a local position relative to a map, an exact position relative to lane of a road, vehicle heading, velocity, etc.) of the vehicle 12 relative to the environment. The guidance system 236 processes sensor data along with other data to determine a path for the vehicle 12 to follow (i.e., path planning data). The vehicle control system 238 generates control signals for controlling the vehicle 12 according to the determined path.

Controls device 222 may include a microprocessor such as a central processing unit (CPU) or graphics processing unit (GPU) in communication with various types of computer readable storage devices or media. Computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the CPU is powered down. Computer-readable storage devices or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controls device 222 in controlling the vehicle. In various embodiments, the vehicle controls device 222 implements machine learning techniques to assist the functionality of the vehicle controls device 222, such as feature detection/classification, obstruction mitigation, route traversal, mapping, sensor integration, ground-truth determination, and the like.

The output of vehicle controls device 222 is communicated to actuators 230. In an exemplary embodiment, the actuators 230 include a steering control, a shifter control, a throttle control, and a brake control. The steering control may, for example, control a steering system 216 as illustrated in FIG. 2. The shifter control may, for example, control a transmission 214 as illustrated in FIG. 2. The throttle control may, for example, control a propulsion system 213 as illustrated in FIG. 2. The brake control may, for example, control wheel brakes 217 as illustrated in FIG. 2.

Method

Figure 4:
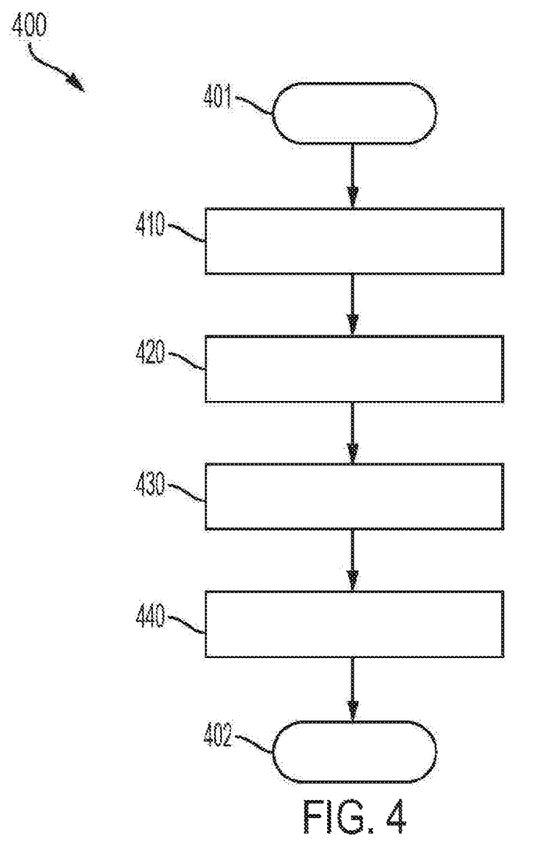
FIG. 4 is a flow chart for an exemplary methodology to initiate remote control of a vehicle according to one aspect of the system and method presented herein.

Now turning to FIG. 4, there is shown an embodiment of a method 400 to enabled restricted area entrance. One or more aspects of the entrance method 400 may be carried out through the vehicle telematics unit 24 and data center 18. One or more ancillary aspects of method 400 may be carried out through a vehicle controls device 222, telematics unit 24, and mobile computing device 57. Skilled artisans will moreover see that telematics unit 24 and data center 18 may be remotely located from each other.

Method 400 is supported by telematics unit 24 being preconfigured to communicate with data center 18 and mobile computing device 57. This configuration may be made by a vehicle manufacturer at or around the time of the telematics unit's assembly or after-market (e.g., via vehicle download using the afore-described communication system (see FIG. 1) or at a time of vehicle service, just to name a couple of examples) and the communications may be cellular communications via wireless carrier system 14 or they may be short-range wireless communications (e.g., Bluetooth, BLE, NFC, RFID, Wi-Fi, etc.). In at least one implementation, one or more executable instructions are provided to the telematics unit 24 and stored on nontransitory computer-readable medium. Method 400 is further supported by preconfiguring data center 18 to remotely control the operations of vehicle 12, for example, to cause the vehicle 12 to traverse from a first location to a second location. Computer 15 may also be preconfigured to store one or more other APIs to support the carrying out one or more steps of method 400.

Method 400 begins at 401 in which vehicle 12 is autonomously traversing along a roadway from one location to another. As follows, the vehicle is relying on controller 222 and ADS 224 to navigate the terrain of the roadway as well as the surrounding traffic to get to its destination. In step 410, using telematics unit 24, vehicle 12 transmits a message to data center 18 that indicates a manual driving sequence should be initiated by an advisor 58, to allow the advisor 58 to remotely control the vehicle 12 (i.e., the controller 222). As follows, during the manual driving sequence, the advisor 58 will be able to take control of the vehicle systems so they can steer and navigate the vehicle 12 around traffic, obstacles, and along roadways to reach the designated destination.

In one situation, the indication message of step 410 may be made upon a direct or indirect request of a vehicle passenger. For example, the vehicle passenger may press one of the buttons and/or controls 30 to initiate a voice communication channel with data center 18 so that they can verbally request an advisor 58 begin remotely controlling vehicle 12. Alternatively, there may be a designated button/ control 30 installed in the vehicle 12 that, once pressed, tells an advisor 54 to automatically, expeditiously, and seamlessly take control of vehicle 12 for emergency purposes without there being an established voice communication channel (i.e., an emergency button).

In another example, a mobile computing device 57 (such as a smart watch) of one of the vehicle passengers may use one or more of its biometric sensing devices to sense that the passenger is in failing health (i.e., the passenger in need of immediate medical attention, unconscious or otherwise comatose, is severely dehydrated, or has an inordinate amount of a foreign substance in their blood). At this point, the mobile computing device 57 may communicate with telematics unit 24 and tell the telematics unit 24 to relay a message to data center 18 that states the advisor shall begin remotely controlling vehicle 12 because one of the vehicle passengers is in failing health and likely needs to get to an emergency services provider as quickly as possible. The message may also indicate that the advisor is to direct the vehicle 12 to an emergency service provider (e.g., a hospital, urgent care, etc.). Generating and transmitting an indication message in this manner may be especially useful when the vehicle 12 has both a manual mode and an autonomous mode. For instance, when one of the vehicle passengers is acting as the driver by operating the vehicle 12 in manual mode. It has also been envisioned that the biometrics sensing device may be installed in the vehicle interior and not on a mobile computing device (e.g., one or more sensing devices installed in the vehicle's steering wheel, seats, seat belts, dashboard, etc.). The telematics unit 24 may also provide one or more audible, visual, and tactile warnings within the cabin of the vehicle 12 in an attempt to wake an unconscious vehicle passenger.

In another situation, the indication message of step 410 can be made after a drop in a confidence level of the vehicle's autonomous driving mode. For example, when the driving sensors 226 of the vehicle's autonomous system 224 show that the environment surrounding the vehicle is too difficult/dangerous for the vehicle 12 to navigate on its own. For instance, when the vehicle 12 is attempting to autonomously navigate through a busy construction zone or through rough terrain such as moving along off-road paths and trails. Alternatively, when the vehicle 12 is attempting to drive itself in severe weather conditions such as thunderstorms, hurricanes, and blizzards. In addition, the vehicle 12 may act proactively by communicating with one or more API suites 99 to assist the vehicle 12 in foreseeing that it is or will be entering into an area that could be to difficult for the vehicle 12 to traverse through autonomously and without any additional support. Thus, the vehicle 12 can transmit the indication message at some time before entering into the area expected to be difficult/impossible for the vehicle 12 to navigate on its own.

The indication message of step 410 may also be made after the vehicle 12 can no longer traverse itself from one location to a set destination. For example, when one or more of the VSMs 44 senses that one of the vehicle systems is malfunctioning. For instance, when the ADS 224 senses a malfunctioning in least one component, if not all of, the driving sensors 226, sensor fusion system 232, positioning system 234, guidance system 236, or vehicle control system 238.

In step 420, the indication message is received by the data center 18. In step 430, server 54 of data center 18 initiates the set up of the manual drive sequence and notifies the advisor 54 they are now to take control of the vehicle's operations (i.e., taking over for controller 222). As follows, the data center 18 will remotely transition the vehicle 12 from a fully autonomous driving mode to a remote manual control mode (i.e., a manual drive sequence mode).

In step 440, the advisor takes full control of the vehicle operations and acts as the vehicle's operator. In order to operate the vehicle, moreover, data center 18 can include one or more simulation vehicle interiors having their own steering wheels, gear shifters, gas and brake pedals, and any other component needed to properly operate the vehicle 12 from a far. Moreover, images taken from cameras and other similar sensing devices installed on the body of vehicle 12 may be displayed on screens in these simulation vehicle interiors so as to assist the advisor 54 in remotely operating vehicle 12. Alternatively, the advisor 54 can operate vehicle 12 via a computer at their desk. In this step, in addition, the advisor controls the vehicle operations and traverses the vehicle from one place to a desired destination. After step 440, method 400 moves to completion.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the system and/or method that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

None of the elements recited in the claims are intended to be a means-plus-function element within the meaning of 35 U.S.C. § 112(f) unless an element is expressly recited using the phrase "means for," or in the case of a method claim using the phrases "operation for" or "step for" in the claim.

What is claimed is:

1. A method to initiate remote control of a vehicle, the method comprising:
    controlling the vehicle by a vehicle controls device performing an automated driving system;
    determining, via a processor, an automated driving confidence level;
    transmitting a request for a manual drive sequence to a remotely located data center in response to the automated driving confidence level being less than a threshold;
    receiving, via the processor, an indication that the manual drive sequence being initiated by the remotely located data center; and
    based on the indication, via the processor, initiating the manual drive sequence such that the remotely located data center can remotely control the vehicle.

2. The method of claim 1, wherein the manual drive sequence enables an advisor to remotely control the vehicle from the remotely located data center.

3. The method of claim 1, wherein the automated driving confidence level is determined in response to an upcoming area considered unsafe for autonomous driving.

4. The method of claim 1, wherein the automated driving confidence level is determined in response to the vehicle attempting to navigate a construction zone.

5. The method of claim 1, wherein the automated driving confidence level is determined in response a malfunction of the vehicle.

6. The method of claim 1, wherein the automated driving confidence level is determined in response to the vehicle attempting to navigate an off-road path.

7. The method of claim 1, wherein the indication is provided by the automated driving system, wherein the indication corresponds to the driving conditions of an environment surrounding the vehicle.

8. A system to initiate remote control of a vehicle, the system comprising:
    a memory configured to comprise one or more executable instructions and a processor configured to execute the executable instructions, wherein the executable instructions enable the processor to carry out the following steps:
        controlling the vehicle by a vehicle controls device performing an automated driving system;
        determining an automated driving confidence level;
        transmitting a request for a manual drive sequence to a remotely located data center in response to the automated driving confidence level being less than a threshold;
        receiving an indication that the manual drive sequence being initiated by a remotely located data center; and
        based on the indication, initiating the manual drive sequence such that the remotely located data center can remotely control the vehicle.

9. The system of claim 8, wherein the manual drive sequence enables an advisor to remotely control the vehicle from the remotely located data center.

10. The system of claim 8, wherein the automated driving confidence level is determined in response to an upcoming area considered unsafe for autonomous driving.

11. The system of claim 8, wherein the automated driving confidence level is determined in response to the vehicle attempting to navigate a construction zone.

12. The system of claim 8, wherein the automated driving confidence level is determined in response a malfunction of the vehicle.

13. The system of claim 8, wherein the automated driving confidence level is determined in response to the vehicle attempting to navigate an off-road path.

14. The system of claim 8, wherein the indication is provided by the automated driving system, wherein the indication corresponds to the driving conditions of an environment surrounding the vehicle.

15. A non-transitory and machine-readable medium having stored thereon executable instructions adapted to initiate remote control of a vehicle, which when provided to a processor and executed thereby, causes the processor to carry out the following steps:
   controlling the vehicle by a vehicle controls device performing an automated driving system;
   determining an automated driving confidence level;
   transmitting a request for a manual drive sequence to a remotely located data center in response to the automated driving confidence level being less than a threshold;
   receiving an indication that the manual drive sequence being initiated by the remotely located data center; and
   based on the indication, initiating the manual drive sequence such that the remotely located data center can remotely control the vehicle.

16. The non-transitory and machine-readable medium of claim 15, wherein the manual drive sequence enables an advisor to remotely control the vehicle from the remotely located data center.

17. The non-transitory and machine-readable medium of claim 15, wherein the automated driving confidence level is determined in response to an upcoming area considered unsafe for autonomous driving.

18. The non-transitory and machine-readable medium of claim 15, wherein the automated driving confidence level is determined in response to the vehicle attempting to navigate a construction zone.

19. The non-transitory and machine-readable medium of claim 15, wherein the automated driving confidence level is determined in response to the vehicle attempting to navigate an off-road path.

20. The non-transitory and machine-readable medium of claim 15 wherein the indication is provided by the automated driving system, wherein the indication corresponds to the driving conditions of an environment surrounding the vehicle.

* * * * *